US011351713B2

(12) United States Patent
Mueller et al.

(10) Patent No.: US 11,351,713 B2
(45) Date of Patent: Jun. 7, 2022

(54) PLANT FOR PRODUCING BEVERAGE CONTAINERS WITH STERILISATION OF THE BLOW MOULDING MACHINE

(71) Applicant: KRONES AG, Neutraubling (DE)

(72) Inventors: Holger Mueller, Pentling (DE); Florian Geltinger, Donaustauf (DE); Juergen Soellner, Beratzhausen (DE)

(73) Assignee: KRONES AG

( * ) Notice: Subject to any disclaimer, the term of this patent is extended or adjusted under 35 U.S.C. 154(b) by 247 days.

(21) Appl. No.: 16/628,612

(22) PCT Filed: Jun. 22, 2018

(86) PCT No.: PCT/EP2018/066709
§ 371 (c)(1),
(2) Date: Jan. 3, 2020

(87) PCT Pub. No.: WO2019/007704
PCT Pub. Date: Jan. 10, 2019

(65) Prior Publication Data
US 2020/0215739 A1    Jul. 9, 2020

(30) Foreign Application Priority Data

Jul. 3, 2017    (DE) ..................... 10 2017 114 766.7

(51) Int. Cl.
*B29C 49/42*    (2006.01)
*B29C 49/46*    (2006.01)
(Continued)

(52) U.S. Cl.
CPC ............ *B29C 49/4252* (2013.01); *A61L 2/18* (2013.01); *A61L 2/20* (2013.01); *B29C 49/46* (2013.01);
(Continued)

(58) Field of Classification Search
CPC . B29C 49/46; B29C 49/4252; B29C 49/6418; B29C 2049/4635; B29C 2049/4611; B29C 2049/4697
See application file for complete search history.

(56) References Cited

U.S. PATENT DOCUMENTS

| 8,453,419 B2 | 6/2013 | Roithmeier et al. ............ 53/426 |
| 8,771,584 B2 | 7/2014 | Voth .............................. 264/535 |

(Continued)

FOREIGN PATENT DOCUMENTS

| DE | 102012108978 | 3/2014 | ............... A61L 2/00 |
| DE | 102013102393 | 9/2014 | ............... A61L 2/16 |

(Continued)

OTHER PUBLICATIONS

German Search Report (w/machine translation) issued in application No. 10 2017 114 766.7, dated Apr. 20, 2018 (12 pgs).
(Continued)

*Primary Examiner* — Robert B Davis
(74) *Attorney, Agent, or Firm* — Hayes Soloway P.C.

(57) ABSTRACT

Apparatus for producing containers, and in particular beverage containers, having a heating device configured to heat plastic parisons, having at least one first transport device, which transports the plastic parisons along a predetermined transport path, a sterilization device configured to sterilize the plastic parisons, and a forming device arranged downstream of the sterilization device, as seen in a transporting direction of the plastic parisons, and configured to form the plastic parisons into plastic containers by the application of a free-flowing medium, wherein said forming device has a transport chamber within which the plastic parisons are transported. The apparatus has an application device configured to apply a free-flowing sterilization medium, at least temporarily, to the transport chamber.

18 Claims, 2 Drawing Sheets

(51) Int. Cl.
*B29C 49/64* (2006.01)
*A61L 2/18* (2006.01)
*A61L 2/20* (2006.01)
*B65B 55/10* (2006.01)
*B67C 3/22* (2006.01)
*B67C 7/00* (2006.01)
*B29L 31/00* (2006.01)

(52) U.S. Cl.
CPC .......... *B29C 49/6418* (2013.01); *B65B 55/10* (2013.01); *B67C 3/22* (2013.01); *B67C 7/00* (2013.01); *A61L 2202/23* (2013.01); *B29C 2049/4635* (2013.01); *B29L 2031/7158* (2013.01); *B67C 2003/227* (2013.01)

(56) References Cited

U.S. PATENT DOCUMENTS

| | | | | |
|---|---|---|---|---|
| 9,327,442 | B2 | 5/2016 | Engelhard et al. ..... | B29C 49/36 |
| 9,409,661 | B2 | 8/2016 | Adriansens ............ | B65B 3/022 |
| 9,919,469 | B2 | 3/2018 | Handschuh et al. ........................ | B29C 49/4289 |
| 2013/0040009 | A1* | 2/2013 | Laumer .................. | B29C 49/46 425/182 |
| 2013/0078327 | A1* | 3/2013 | Adriansens ............ | B29C 49/68 425/210 |
| 2013/0133297 | A1* | 5/2013 | Adriansens ............ | B29C 49/68 53/558 |
| 2014/0260099 | A1* | 9/2014 | Braum .................. | B65B 55/027 53/432 |
| 2016/0325482 | A1 | 11/2016 | Hayakawa et al. ..... | B29C 49/46 |

FOREIGN PATENT DOCUMENTS

| | | | | |
|---|---|---|---|---|
| DE | 102013110088 | 3/2015 | ............ | B29C 49/42 |
| EP | 2295324 | 3/2011 | ............ | B29C 49/42 |
| EP | 2412511 | 2/2012 | ............ | B29C 49/42 |
| EP | 2468478 | 6/2012 | ............ | B29C 31/00 |
| EP | 2623293 | 8/2013 | ............ | B29C 49/42 |

OTHER PUBLICATIONS

International Preliminary Report on Patentability (w/translation) issued in application No. PCT/EP2018/066709, dated Jan. 7, 2020 (24 pgs).

International Search Report and Written Opinion (w/translation) issued in application No. PCT/EP2018/066709, dated Oct. 26, 2018 (33 pgs).

* cited by examiner

PLANT FOR PRODUCING BEVERAGE CONTAINERS WITH STERILISATION OF THE BLOW MOULDING MACHINE

BACKGROUND OF THE INVENTION

The present invention relates to a device and a method for establishing producing beverage containers. Such methods have been known for a long time from the prior art. In a known method first of all plastic parisons are heated, then sterilised, then reshaped into plastic containers by means of a reshaping device, such as for example a stretch blow moulding machine, and finally in this reshaped state are preferably filled with a liquid and in particular a beverage. In this case, depending upon the beverage to be introduced, different degrees of sterilisation or cleanness are known. Thus, more recently, sterile blow moulding machines have also become known from the prior art, which facilitate production of plastic bottles under sterile or clean room conditions. Such machines are developed according to all aseptic and hygiene criteria with regard to process engineering and process design.

However, products also exist, which can be filled subject to lower hygienic requirements. For these products production plants have been developed which, in contrast to the completely aseptic transport path after container disinfection or parison disinfection up to the filing process, function with a non-sterile or conventional blow moulding machine instead of a sterile blow moulding machine. In such cases it is known from the internal prior art of the applicant that here only conditioned air, for example filtered and dried air, is fed to the blow moulding machine, in order to keep potentially impure air away from the module and also in order to avoid water condensation in the blow moulding module or the blow moulding machine. In this case the different machines are usually designed appropriately for each application. However, there is sometimes a need for a machine type which does not necessarily offer the very elaborate completely sterile transport path, but on the other hand also provides a higher degree of cleanness than completely non-aseptic plants.

Therefore the object of the present invention is to provide a device and a method which on the one hand still offer an acceptable degree of purity of the produced containers, but on the other hand are not necessarily kept completely sterile and in this way are more advantageous to produce and/or to operate.

SUMMARY OF THE INVENTION

A device according to the invention in this connection for producing containers, and in particular beverage containers, has a heating device which is suitable and intended for heating plastic parisons. Furthermore, the device has a first transport device, which transports these plastic parisons along a predetermined transport path, and a sterilising device which is suitable and intended for sterilising the plastic parisons. Furthermore, the device has a reshaping device which is arranged after the sterilising device in one transport direction of the plastic parisons and is suitable and intended for reshaping the plastic parisons into plastic containers by the application of a flowable medium. In this case this reshaping device has a transport area inside which the plastic parisons are transported.

According to the invention the device has an application device which applies a flowable sterilising medium to this transport area at least intermittently and preferably permanently. The application device preferably also applies the medium to the transport area during the production. This application is preferably an application of gas.

The said reshaping device is in particular a blow moulding machine and particularly preferably a stretch blow moulding machine. In this case this reshaping device preferably has blow moulds which are arranged on the individual reshaping stations. In this case these blow moulds are preferably arranged at least indirectly on blow mould supports and can be opened and closed by means of these blow mould supports. Furthermore, the individual transforming stations preferably each have rod-like bodies which can be introduced into the plastic parisons in order expand them in the longitudinal direction. The reshaping device preferably has a rotatable support, the so-called blow moulding wheel, on which a plurality of transforming stations are arranged.

In this case it is possible that the said reshaping device has a clean room, inside which the plastic parisons are transported and reshaped. Preferably, however, this machine has no such clean room and thus preferably is not designed to be aseptic.

However, this reshaping device preferably has a housing inside which the plastic parisons are transported and/or reshaped. In this case this housing can have substantially two openings, wherein the plastic parisons are transported through one of these openings into the reshaping device and as reshaped bottles are transported again through a second opening and out of the reshaping device.

The invention proposes to create a certain sterilising medium atmosphere inside the reshaping device in order in this way to increase the degree of cleanness in the reshaping device. In this case the medium can preferably be applied to components of the reshaping device, for instance the blow moulds, the supports thereof or the like. In addition, however, it is preferable that only one sterilising medium atmosphere is created in the area.

In a preferred embodiment the device has an application device, which applies a flowable medium to the plastic parisons reshaping and/or expansion thereof. This flowable medium can in particular be air, in particular blowing air or sterile air, which is blown into the plastic parisons in order to expand them. However, it would also be possible for the flowable medium to be a liquid, in particular the beverage to be introduced which is introduced into the plastic parisons, so that the plastic parisons are also expanded by the product to be introduced. In this case the reshaping device would simultaneously be a reshaping device and also a filling machine.

However, the flowable sterilising medium which is applied to the transport area or the reshaping area may in particular not be exclusively hydrogen peroxide ($H_2O_2$) or peracetic acid.

The heating device which is connected upstream of the reshaping device is preferably a linear oven. The plastic parisons are preferably heated inside this linear oven, and this can take place in particular by infrared heating elements. However, it would also be possible for the oven to be a microwave oven, which heats the plastic parisons by application of microwaves. It would also be possible that the heating device is directly an injection moulding machine, that is to say the plastic parisons originate directly from an injection moulding machine and therefore still have a high intrinsic temperature. At the same time in this case the injection moulding machine would also be the said heating device.

In a further advantageous embodiment, the sterilising device is suitable and intended for applying a sterilising medium and in particular a flowable steilising medium to the interiors of the plastic parisons. Additionally or alternatively, however, it would also be conceivable that this sterilising device has radiation devices which apply radiation at least to sections of the wall of the plastic parisons for the purpose of sterilisation. This radiation can be for example electron radiation.

Preferably in this case this radiation device also acts in particular on an internal surface of the plastic parisons.

In a further advantageous embodiment, the sterilising device is with the reshaping device is in communication with the reshaping device in such a way that a sterilising medium can pass from the sterilising device to the reshaping device. Thus, for example housing parts of the sterilising device and the reshaping device could be connected to one another by means of an opening, wherein the plastic parisons can be transported through this opening.

Therefore, in a further advantageous embodiment the concentration of the sterilising medium inside the sterilising module or inside the sterilising device is higher than in the reshaping device. The sterilising medium can in particular enter the reshaping device through an air lock from the sterilising device. Thus, here this air lock constitutes the application device which is suitable and intended for applying the sterilising medium to the transport area of the reshaping device.

Advantageously therefore the sterilising device also has a housing or a housing area, inside which the sterilisation of the plastic parisons takes place. Furthermore, an application device is preferably also provided, which applies a sterilising medium to the sterilising device and in particular also to this sterilising area.

Therefore, it is proposed that the reshaping device is exposed to a sterilising atmosphere using a low sterilising medium concentration. It is known for example that laboratories, warehouses or other facilities are sterilised with low $H_2O_2$ concentrations, without having to pay attention to the $H_2O_2$ resistance of the gas-treated materials. These materials remain in the areas during the sterilisation. In this case the slight atmosphere is not corrosive and the successful sterilisation is achieved by a long treatment period.

Preferably at least components of the reshaping device and particularly preferably the reshaping device itself are permanently acted upon, in particular also permanently during the production, with low concentrations of sterilising media and in particular are gas-treated, for example with $H_2O_2$. With such a method no structural changes have to be carried out on the reshaping device, in particular since small concentrations of the sterilising medium do not have a corrosive effect.

Preferably, therefore, the application device is configured in such a way that a sterilising medium is applied to the transport area and/or devices inside this transport area in a concentration which is lower than the sterilisation by the sterilising medium in the sterilising device. Advantageously this concentration is less than 1,000 ppm, preferably less than 800 ppm, preferably less than 700 ppm, preferably less than 600 ppm and particularly preferably less than 500 ppm. This concentration is particularly preferably greater than 30 ppm, preferably greater than 40 ppm and preferably greater than 50 ppm.

The procedure also has the advantage that the sterilising medium, which already to a certain extent results as a waste product in the sterilising device, can be used in order to sterilise the reshaping device. Thus, for example the application device can have an exhaust air flap, which is arranged in particular between the sterilising device and the reshaping device. By means of this exhaust air flap the sterilising medium can enter the reshaping device from the sterilising device.

Thus, in this preferred embodiment the sterilising medium, for example the $H_2O_2$ gas, can be provided by means of an intentional outflow of the treatment gas from the sterilising device. In this case the said exhaust air flap between the sterilising device and the reshaping device can be regulated in such a way that due to a slight positive pressure inside the entire plant the sterilising medium, for example the sterilising gas, is forced or pushed in the direction of the reshaping device. In this way there is no additional consumption of $H_2O_2$, but in fact the gas already used for treating the plastic parisons is also used secondarily for a surface sterilisation of the reshaping device and thus is recycled.

In a further advantageous embodiment, the device or the application device has a control device which controls or regulates a flow of the sterilising medium from the sterilising device to the reshaping device. In this case, if required, this control device can preferably control or regulate the amount of sterilising medium which reaches the reshaping device.

Therefore, in a further preferred embodiment the application device has an exhaust air flap which is arranged between the sterilising device and the reshaping device.

In a further advantageous embodiment, the device has a filling device which is arranged after the reshaping device in the transport direction of the plastic containers. In this case this filing device serves in particular for filling the now finished plastic containers with a liquid and in particular with a beverage.

In a further advantageous embodiment, the device has an extracting device in order to extract a gaseous medium from the transport area of the reshaping device. Using this procedure it is also possible to ensure that no sterilising medium reaches the filling device. Furthermore, it is also possible that filtered and/or dried air is fed to the reshaping device, and this preferably takes place in addition to the feeding of sterilising medium. A ventilation circuit can also be achieved inside the reshaping device due to the extraction of a flowable and in particular gaseous medium from the reshaping device.

Advantageously a flow of the sterilising medium and/or the air in the interior of the transport area is also proposed. In a further advantageous embodiment, a further sterilising device is also provided which supplies the filling device with a gaseous medium and in particular with air. Advantageously in this case this ventilation device can have elements, such as for instance pre-filters, air dryers or temperature controllers, so that it is possible to feed filtered and/or dried air to the reshaping device. In a preferred embodiment, devices are provided which prevent escape of the sterilising medium from the reshaping device to the filling device. Thus for example in a region of the housing, and in particular a region of the housing in which the plastic bottles exit again from the reshaping device, a circumferential and/or slotted pipe or a channel could be provided, by means of which the gas atmosphere is for example extracted by means of an exhaust air fan.

In a further advantageous embodiment, the reshaping device has a temperature measuring device. It is preferably possible that the application device for the sterilising medium, for example an exhaust air flap, can also be controlled and/or regulated as a function the temperature measured inside the reshaping device. Thus, for example as a function of this measured temperature a concentration can be regulated by means of the pressure difference between the sterilising device and the reshaping device. Thus, for example it would also be possible that during a change of blow mould a higher concentration of sterilising medium is regulated in the reshaping device and in this way the blow moulds are also additionally sterilised. In addition, it would also be possible that the blowing air paths are also sterilisable in particular with low gas concentrations or sterilising medium concentrations.

In the manner described here it is possible, without a great outlay on construction, to bring a standard reshaping device or standard blow moulding machine to a hygienically high level. Since the $H_2O_2$ gas used for sterilisation of the reshaping device is already present, no higher costs or material consumption also ensue.

In a further advantageous embodiment, the device has a conditioning device for conditioning of at least one medium to be fed to the device and in particular a temperature control device for controlling the temperature of at least one medium to be fed to the device.

As mentioned, a permanent gas treatment with sterilising medium and in particular evaporated $H_2O_2$ is proposed for the blow moulding module or the reshaping device. Since in the blow moulding module a precise and in particular very precise setting of the $H_2O_2$ concentration is, on the one hand, important for the maintenance of the low-germ state (the concentration should not be too low) and, on the other hand, for the service life of the plant (the concentration should not be too high, so that components such as for example non-ferrous metals do not corrode), in this embodiment it is proposed to ensure the $H_2O_2$ concentration by means of conditioning and in particular by means of a dew point regulation.

Therefore the temperature control device preferably performs a dew point regulation and in particular a dew point regulation of the gaseous medium to be fed to the reshaping device.

In a particularly preferred embodiment, the conditioning device is at least intermittently in communication with the reshaping device and in particular the transport area of the reshaping device. In this case this communication can take place in particular by means of connecting conduits.

In a preferred embodiment the conditioning device has at least one heat exchanger device. Particularly preferably this heat exchanger device is controllable and/or regulable, so that in particular the temperature of the sterilising medium (such as in particular the $H_2O_2$) entering the reshaping device can be regulated.

In a further embodiment the conditioning device has a dehumidifier. The said heat exchanger device is preferably the dehumidifier.

In a further preferred embodiment, the conditioning device has at least one temperature measuring device in order to determine a temperature. In this case this may in particular be a temperature in an inner area of the reshaping device.

However, it would also be (alternatively or additionally) possible that a temperature of the sterilising medium to be fed to the reshaping device is measured. Thus, for instance the temperature of the sterilising medium in a feed conduit for the sterilising medium could be measured. The temperature in the interior area of the reshaping device could also be measured.

In this case a high gas concentration, such as is known for disinfection of packaging means, is preferably generated. This gas is temperature-controlled and in particular cooled by means of a dehumidifier to a required temperature in order to adjust the excess $H_2O_2$ concentration through the saturation.

In one embodiment a heat exchanger has a temperature control medium passed through it which condenses $H_2O_2$ to saturation point and can be discharged. Thus a concentration of $H_2O_2$ which is neither too low nor too high is applied to the blow moulding module or the reshaping device.

Several variants are possible for this procedure. Thus it would be conceivable for the sterilising medium, such as for instance $H_2O_2$, to be removed directly from the fed treatment air and to be conditioned by means of a dehumidifier. As stated above, a temperature measurement could take place either in the feed conduit or directly in the interior area of the blow moulding machine.

In a further variant the $H_2O_2$ is removed at the extraction point after the treatment module and is fed (preferably by means of a fan) via the dehumidifier and a feeder into the blow moulding module or the reshaping device.

The advantage of the temperature measurement in the interior area of the blow moulding machine is that the mixing temperature, which results from the mixture between treatment air and fed air from the ventilation technology, is recorded. In this way a subsequent cooling and thus condensation of the sterilising medium can be ruled out.

Furthermore, the present invention is directed to a method for producing beverage containers, wherein plastic parisons are heated by means of a heating device and after this heating are transported to a sterilising device and are sterilised there by means of this sterilising device. Furthermore, the plastic parisons are transported from this sterilising device to a reshaping device and from this reshaping device are expanded into plastic containers and in particular plastic bottles by application of a flowable medium. In this case, while the plastic parisons and in particular plastic bottles are being expanded they are transported through a transport area of the reshaping device. According to the invention a flowable sterilising medium is applied at least intermittently to this transport area of the reshaping device and/or components inside this transport area.

In a preferred method a sterilising medium flows at least temporarily from the sterilising device to the reshaping device. In this case, therefore, a sterilising medium originating from the sterilising device is applied to the reshaping device.

In a further preferred method, the sterilising medium is extracted at least temporarily from the transport area of the reshaping device.

In a further preferred method, the flowable medium, in particular the sterilising medium, is at least temporarily conditioned and in particular temperature-controlled. This conditioning and in particular temperature control takes place particularly preferably by means of a heat exchanger device. Particularly preferably, the heat exchanger device is a gas-operated or a liquid-operated heat exchanger device.

A dew point of the sterilising medium is particularly preferably regulated. Particularly preferably the sterilising gas is cooled by means of a dehumidifier to a predetermined temperature. Particularly preferably a concentration and in particular an $H_2O_2$ concentration can be set by the saturation.

Particularly preferably a temperature of the sterilising medium and/or of the interior of the reshaping device is at least intermittently measured. In a further preferred method, the conditioning device is controlled on the basis of these temperature measurements.

BRIEF DESCRIPTION OF THE DRAWINGS

Further advantages and embodiments are disclosed by the appended drawings. In the drawings.

DETAILED DESCRIPTION OF THE INVENTION

Figure 1:
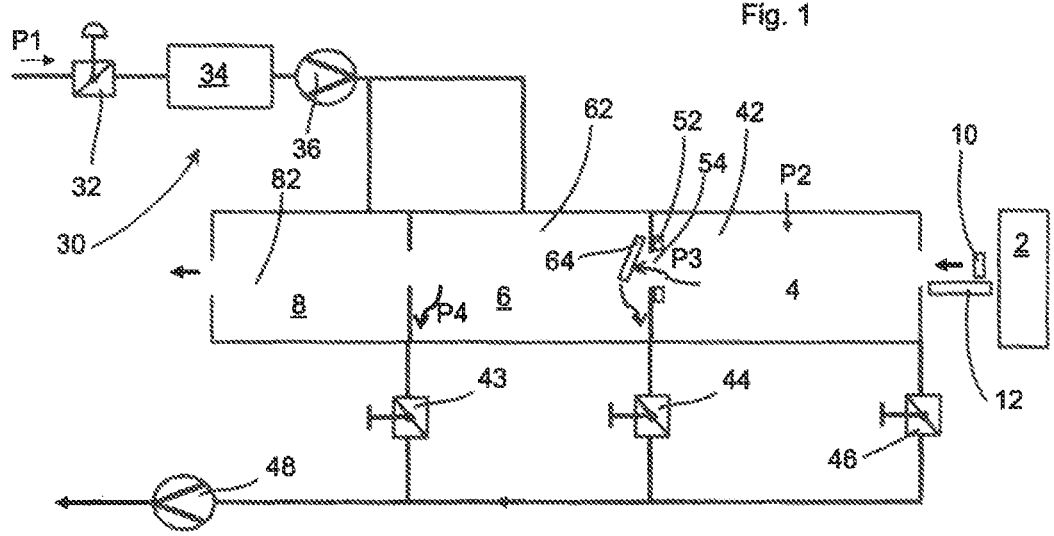
FIG. 1 shows a schematic representation of a plant according to the invention for producing beverage containers.

FIG. 1 shows a schematic representation of a device 1 according to the invention for producing beverage containers. In this case the reference 2 relates to a heating device which is suitable and intended for heating plastic parisons 10. A transport device 12 then transports the plastic parisons 10 in a heated state first of all to a sterilising device 4. It is pointed out that the transport device also extends substantially through the entire plant. This transport device can also have a plurality of transport units, such as for example transport starwheels, transport belts and the like, which extend through the entire plant. The blow moulding wheel mentioned above but not shown in the drawing may also be such a transport device.

Inside the sterilising device a sterilising medium, for example an $H_2O_2$ gas, is applied to the plastic parisons. The reference 42 designates a transport area within which the plastic parisons are transported during their sterilisation. This transport area 42 is acted upon by an atmosphere of the sterilising medium, as indicated by the arrow P2. The reference 6 designates a reshaping device, inside which the plastic parisons are reshaped into the plastic bottles by expansion or application of blowing air.

In this case this reshaping device likewise has a transport area 62, within which a transport device which transports the plastic parisons is likewise arranged. In this case this transport device is designed in particular as a blow moulding wheel (not shown), on which a plurality of reshaping stations are arranged. In this case these reshaping stations in each case serve for reshaping the plastic parisons into plastic containers. For this purpose, the blow moulding wheel rotates and thus the plastic parisons are expanded in a carousel operation. In this case, as mentioned above, the individual reshaping stations preferably have blow mould supports on which blow mould parts are arranged at least indirectly.

The reference P3 designates a passage of the sterilising medium from the transport area 42 of the sterilising device 4 into the transport area 62 of the reshaping device 6. For this purpose, the reference 64 designates a ventilation flap which can be opened or more or less closed in order in this way to be able to control or regulate the passage of the sterilising medium from the sterilising device 4 to the reshaping device 6.

The reference 8 designates a filling device by which the containers now shaped by the transforming device 6 are filled with a filling material and in particular a beverage. For this purpose the filling device 8 likewise has a transport area 62, inside which the plastic containers are transported during the filling. Advantageously the filing device can also have a filling wheel on which a plurality of filling stations are arranged, wherein each of these filling stations is suitable and intended for filling the plastic bottles with a beverage.

In this case, as mentioned above, in the sterilising device or the transport area 42 a higher level or a greater concentration of sterilising medium prevails than in the transport area 62 of the reshaping device 6. Preferably, there should also be no sterilising medium atmosphere prevailing in the transport area 82 of the filling device or the concentration there should be substantially 0.

Furthermore, the machine has a ventilation device 30 which serves for ventilation in particular of the reshaping device 6 and the filling device 8. In this case the ventilation device 30 first of all has a valve device 32 to which feed air (arrow P1) is fed. The reference 34 designates an air conditioning unit, in particular a unit which can have a pre-filter, an air dryer and a temperature control unit. The gas or the air which is thus preconditioned is fed by means of a fan 36 both to the filling device 8 and also to the reshaping device 6.

The references 43, 44 and 46 designate valve devices which can regulate an extraction of media from the individual stations, that is to say the sterilising device 4, the reshaping device 6 and the filling device 8. Finally, the reference 48 designates an extractor such as a fan or pump which serves in order to be able to discharge the air. Within the context of this control of these individual valves 42, 44 and 46 it is possible in particular to control or regulate to what extent, or on what scale, air or also air containing sterilising medium can be discharged from the individual devices.

The reference 52 designates a special extracting device, which is arranged on an outlet 54 of the reshaping device and which in particular serves in order to extract sterilising medium in this region. In this way it is possible to prevent sterilising medium or residues of sterilising medium from entering the filling device.

In this case, as mentioned above, this extracting device is designed as a circumferential pipe or channel, which is preferably slotted, and which particularly preferably can discharge the gas atmosphere from the reshaping device 6 by means of the exhaust air fan 48 which is already present.

Figure 2:
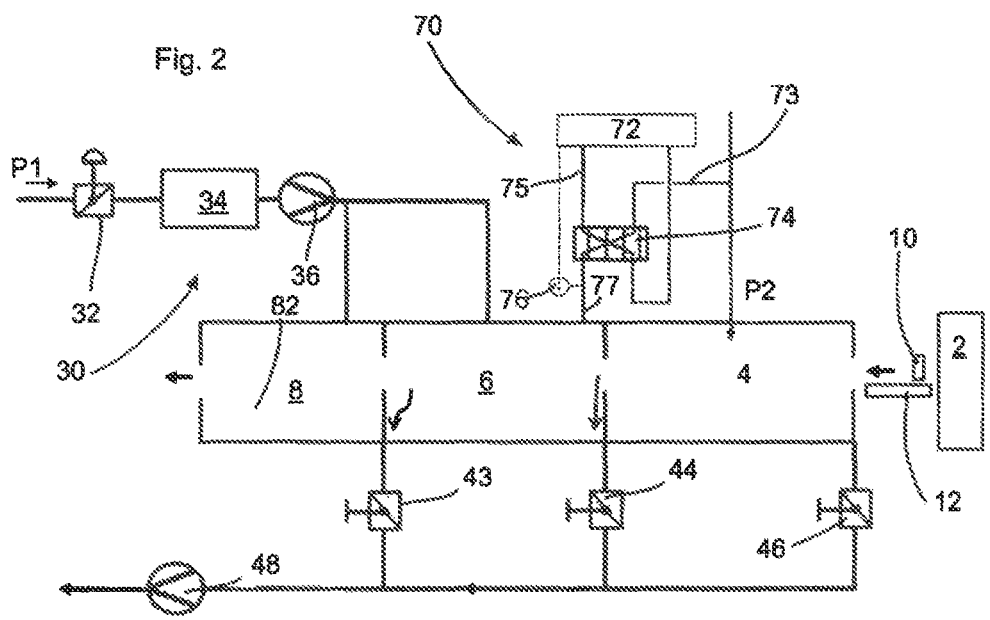
FIG. 2 shows a plant with a conditioning device in a first embodiment.

FIG. 2 shows a further embodiment of a plant according to the invention. In this embodiment the plant has a conditioning and in particular temperature control device, designated in its entirety by 70, for the sterilising medium to be fed to the reshaping device 6.

This temperature control device has a heat exchanger device 74, to which the sterilising medium is fed by means of a feed conduit 73. In this case this feed conduit 73 can be branched off from a main conduit, but can also open directly into this heat exchanger.

The reference numeral 72 designates a control device for the heat exchanger device 74. This controls in particular the temperature of a temperature control medium which is fed by means of a conduit 75 to the heat exchanger device 74.

The reference 76 designates a temperature measuring device, which determines a temperature of the sterilising medium in the conduit 77.

Figure 3:
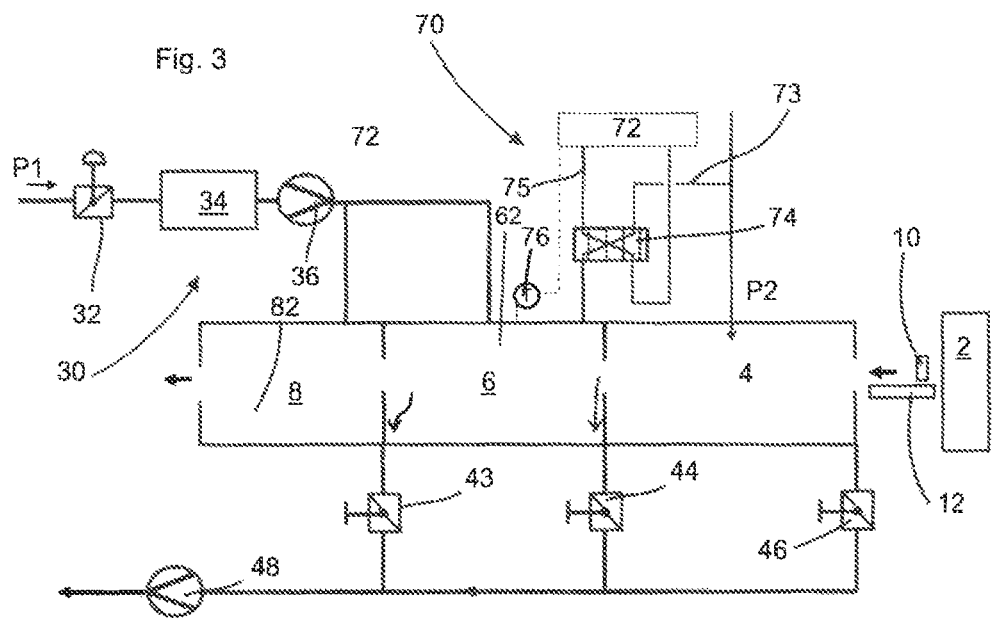
FIG. 3 shows a plant with a conditioning device in a second embodiment.

FIG. 3 shows a further embodiment of the plant shown in FIG. 2, which differs in particular by the arrangement of the temperature measuring device. In this embodiment the temperature measuring device 76 measures the temperature directly in the area 62 of the reshaping device. In both embodiments the conditioning device is also controlled having regard to the measured temperature.

Figure 4:
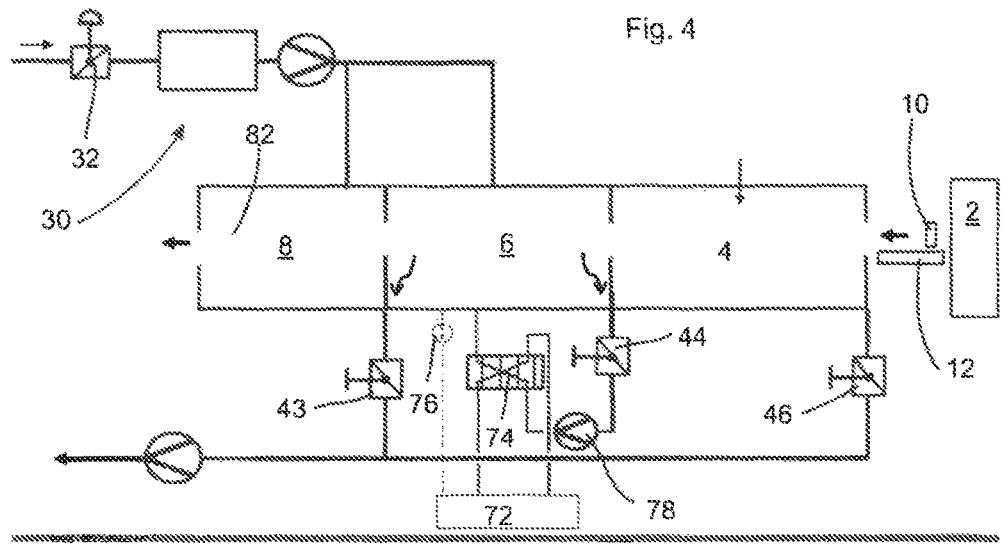
FIG. 4 shows a plant with a conditioning device in a third embodiment.

In a further embodiment it would also be possible for two or more temperature measuring devices to be provided, for instance at the position as shown by FIG. 2 and FIG. 3. FIG. 4 shows a further embodiment of the plant according to the invention with conditioning device. In this embodiment sterilising medium is removed from the treatment module and is fed by means of a fan device 78 to the reshaping device 6. The heat exchanger device operates here in the same manner as described above.

The applicant reserves the right to claim all the features disclosed in the application documents as essential to the invention in so far as they are individually or in combination novel over the prior art. Furthermore, it is pointed out that features which may be advantageous per se have also been described in the individual drawings. The person skilled in the art recognises immediately that a specific feature described in a drawing may also be advantageous without the incorporation of further features from this drawing. Furthermore, the person skilled in the art recognises that advantages may also result from a combination of several features shown in individual drawings or in different drawings. Furthermore, it is pointed out that features, which are described here with reference to the device are also used with regard to the method which is likewise described.

LIST OF REFERENCES 2 heating device
4 sterilising device
6 reshaping device
8 filling device
10 plastic parisons
12 transport device
30 ventilation device
32 valve device
34 air conditioning unit
36 fan
42 transport area
43 valve device
44 valve device
46 valve device
48 extracting device, exhaust air fan
52 extracting device
54 outlet of the reshaping device
62 transport area
64 ventilation flap
70 conditioning device
72 control device
73 conduit
74 heat exchanger device
75 conduit
76 temperature measuring device
78 pumping device, fan
82 transport area
P1 feed air
P2 atmosphere of the sterilising medium
P3 passage of the sterilising medium

The invention claimed is:

1. A production device for producing beverage containers with a heating device configured for heating plastic parisons, with at least one first transport device which transports these plastic parisons along a predetermined transport path, with a sterilising device configured for sterilising the plastic parisons and with a reshaping device which is arranged after the sterilising device in a transport direction of the plastic parisons and configured for reshaping the plastic parisons into plastic containers by application of a flowable medium, wherein this reshaping device has a transport area inside which the plastic parisons are transported, wherein the device has an application device configured to apply a flowable sterilising medium to this transport area, wherein the reshaping device has no clean room and thus also is not aseptic, wherein the application device includes an air lock, and the sterilising device is in communication with the reshaping device in such a way that the sterilising medium can pass through the air lock from the sterilising device to the reshaping device, and the production device has a control device for controlling or regulating a flow of the sterilising medium from the sterilising device to the reshaping device, wherein the control device is configured to control or regulate the amount of sterilising medium which reaches the reshaping device.

2. The production device according to claim 1, wherein the sterilising device has an application device configured to apply the flowable sterilising medium to the plastic parisons.

3. The production device according to claim 1, wherein the application device is configured such that sterilising medium is applied to the transport area with a concentration which is lower than a concentration of this sterilising medium in the sterilising device.

4. The production device according to claim 1, wherein the application device has an exhaust air flap arranged between the sterilising device and the reshaping device.

5. The production device according to claim 1, wherein the production device has a filling device which is arranged after the reshaping device in a transport direction of the plastic containers.

6. The production device according to claim 1, wherein the production device has an extracting device configured to extract a gaseous medium from the transport area of the reshaping device.

7. The production device according to claim 1, wherein the production device has a gas application device configured to apply a gas to the reshaping device.

8. The production device according to claim 1, wherein the production device has a conditioning device configured to condition at least one medium to be fed to the device, wherein the conditioning device is preferably in communication at least temporarily with the transport area of the application device.

9. The production device according to claim 8, wherein the conditioning device has at least one heat exchanger device.

10. The production device according to claim 8, wherein the conditioning device has at least one temperature measuring device configured to measure a temperature of the sterilising medium and/or a temperature of the transport area.

11. A method for producing beverage containers, wherein plastic parisons are heated by a heating device and after heating are transported to a sterilising device to be sterilised by the sterilising device and are transported from this sterilising device to a reshaping device and from this reshaping device are expanded into plastic containers, wherein while the plastic parisons are being expanded they are transported through a transport area of the reshaping device, wherein a flowable sterilising medium is at least temporarily applied to this transport area of the reshaping device, wherein the reshaping device has no clean room and thus also is not aseptic, wherein the application device includes an air lock, and the sterilising device is in communication with the reshaping device in such a way that the sterilising medium can pass through the air lock from the sterilising device to the reshaping device, and the production device has a control device for controlling or regulating a flow of the sterilising medium from the sterilising device to the reshaping device, wherein the control device is configured to control or regulate the amount of sterilising medium which reaches the reshaping device.

12. The method according to claim 11, wherein the sterilising medium flows at least temporarily from the sterilising device to the reshaping device and/or the sterilising medium is extracted at times intermittently from the transport area of the reshaping device.

13. The method according to claim 11, wherein at least components of the reshaping device are permanently gas-treated with low concentrations of sterilising media.

14. The method according to claim 11, wherein the flowable medium is at least temporarily conditioned.

15. The production device according to claim 7, wherein the gas application device is configured to supply air to the recharging device.

16. The production device according to claim 8, wherein the conditioning device includes a temperature control device.

17. The method according to claim 11, wherein the beverage containers comprise plastic bottles.

18. The method according to claim 11, wherein the flowable medium is at least temporarily temperature controlled.

* * * * *